United States Patent
Adams et al.

(10) Patent No.: US 11,139,076 B2
(45) Date of Patent: Oct. 5, 2021

(54) SYSTEM, METHOD AND APPARATUS FOR COGNITIVE ORAL HEALTH MANAGEMENT

(71) Applicant: International Business Machines Corporation, Armonk, NY (US)

(72) Inventors: Ebony C. Adams, Austin, TX (US); Michael Bender, Rye Brook, NY (US); Christian Compton, Austin, TX (US); Jeremy R. Fox, Georgetown, TX (US); Manjunath Ravi, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 550 days.

(21) Appl. No.: 15/841,979

(22) Filed: Dec. 14, 2017

(65) Prior Publication Data
US 2019/0139632 A1    May 9, 2019

Related U.S. Application Data

(63) Continuation of application No. 15/806,405, filed on Nov. 8, 2017.

(51) Int. Cl.
*G16H 10/60* (2018.01)
*G16H 15/00* (2018.01)
(Continued)

(52) U.S. Cl.
CPC .............. *G16H 40/63* (2018.01); *G16H 10/60* (2018.01); *G16H 15/00* (2018.01); *G16H 50/20* (2018.01); *G16H 80/00* (2018.01)

(58) Field of Classification Search
CPC ........... A61C 15/04; A61C 9/00; A61C 17/34; G06F 19/321; G06F 19/00; G06F 19/24;
(Continued)

(56) References Cited

U.S. PATENT DOCUMENTS

| | | | |
|---|---|---|---|
| 10,064,711 B1 * | 9/2018 | Richter | .................... A41H 1/02 |
| 2003/0013062 A1 * | 1/2003 | White | ..................... A61C 7/00 |
| | | | 433/21 |

(Continued)

FOREIGN PATENT DOCUMENTS

| | | | | |
|---|---|---|---|---|
| CN | 206133565 U | 4/2017 | | |
| WO | 2013/069008 A1 | 5/2013 | | |
| WO | WO-2017211218 A1 * | 12/2017 | ............. | A61C 17/22 |

OTHER PUBLICATIONS

Tavor, "IBM Watson Tradeoff Analytics—General Availability", https://www.ibm.com/blogs/cloud-archive/2015/05/watson-tradeoff-analytics/, 2015 (Year: 2015).*

(Continued)

*Primary Examiner* — Fonya M Long
*Assistant Examiner* — Alaaeldin M Elshaer
(74) *Attorney, Agent, or Firm* — Scott S. Dobson; Hunter E. Webb; Keohane & D'Alessandro, PLLC (57) ABSTRACT

Approaches presented herein enable cognitive oral health management. Specifically, data from at least one internet of things (IoT) sensor and data from at least one visual image sensor are collected over time for a user via one or more sensors operatively coupled with one or more personal daily oral care devices as the user is performing a periodic oral care activity with the one or more personal daily oral care devices. Collected data are subjected to cognitive diagnostics to identify abnormalities in a user's oral healthcare regimen and physiological abnormalities within the oral cavity by categorizing data. A report for a medical professional may be generated providing recommendation of potential diagnoses and treatment options.

9 Claims, 6 Drawing Sheets

(51) Int. Cl.
*G16H 40/63* (2018.01)
*G16H 50/20* (2018.01)
*G16H 80/00* (2018.01)

(58) Field of Classification Search
CPC ........ G06F 19/26; G16H 10/60; G16H 50/20; G16H 15/00; C12Q 1/68; H04L 29/08; H04L 9/00
USPC .......................................................... 705/2, 3
See application file for complete search history.

(56) References Cited

U.S. PATENT DOCUMENTS

| | | | |
|---|---|---|---|
| 2008/0162352 A1* | 7/2008 | Gizewski | G06Q 50/24 705/50 |
| 2010/0170052 A1 | 7/2010 | Ortins et al. | |
| 2010/0227296 A1 | 9/2010 | Mandelis et al. | |
| 2010/0281636 A1 | 11/2010 | Ortins et al. | |
| 2012/0295216 A1 | 11/2012 | Dykes et al. | |
| 2013/0122468 A1 | 5/2013 | Abrams et al. | |
| 2015/0132707 A1* | 5/2015 | Huang | A61C 7/08 433/6 |
| 2015/0339444 A1* | 11/2015 | Kimmel | H04L 67/32 709/219 |
| 2016/0367188 A1 | 12/2016 | Malik et al. | |
| 2017/0175172 A1* | 6/2017 | Apte | G16B 35/00 |
| 2017/0177811 A1* | 6/2017 | Mcfarland | G16H 10/60 |
| 2018/0168781 A1* | 6/2018 | Kopelman | G16H 50/50 |

OTHER PUBLICATIONS

Appendix P, "List of IBM Patents or Patent Applications Treated as Related", Mar. 26, 2020, 2 pages.
Kathleen Lenau, "Spectral Cytopathology: A Diagnostic Tool for the Oral Cavity and the Esophagus", Northern University, Boston, Masschusetts, May 3, 2013, 72 pages.
ip.com, Authors et. al.: Disclosed Anonymously, "Oral health improving compositions also suited for pet food", IP.com No. IPCOM000205913D, IP.com Electronic Publication Date: Apr. 7, 2011, 99 pages.
ip.com, Authors et. al.: Disclosed Anonymously, "System and Method for generating Medical Images to reflect treatment or progress improvements", IP.com No. IPCOM000224119D, IP.com Electronic Publication Date: Dec. 10, 2012, 7 pages.
Elshaer, Alaaeldin M., U.S. Appl. No. 15/806,405, Office Action dated May 27, 2020, 34 pgs.
Elshaer, Alaaeldin M., U.S. Appl. No. 15/806,405, Final Office Action dated Sep. 29, 2020, 42 pgs.
Elshaer, Alaaeldin M., U.S. Appl. No. 15/806,405, Notice of Allowance dated Apr. 13, 2021, 12 pgs.

* cited by examiner

SYSTEM, METHOD AND APPARATUS FOR COGNITIVE ORAL HEALTH MANAGEMENT

CROSS-REFERENCE TO RELATED APPLICATIONS

The present patent document is a continuation of U.S. patent application Ser. No. 15/806,405, filed Nov. 8, 2017, entitled "SYSTEM, METHOD AND APPARATUS FOR COGNITIVE ORAL HEALTH MANAGEMENT", the disclosure of which is incorporated herein by reference.

TECHNICAL FIELD

This invention relates generally to oral health monitoring and management and, more specifically, to gathering visual and other measurement data over time during a user's utilization of a personal daily oral device, performing an oral health diagnosis on the measurement data and generating a report for a medical professional providing recommendations of potential diagnosis and treatment options.

BACKGROUND

Oral care is of critical importance across the globe. Today, there is no efficient way to regularly and proactively detect if individuals are optimizing their personal oral care or if a dental visit may be required. Dental cleanings, typically performed twice per year for those who can afford them, generally provide only an instantaneous evaluation of the oral health of a patient. A broader spatial and temporal and more proactive view of personal oral care and resulting changes in oral health would be helpful to oral healthcare providers and their patients.

SUMMARY

In general, embodiments described herein provide approaches for performing cognitive oral health management. Specifically, data from at least one internet of things (IoT) sensor and data from at least one visual image sensor are collected over time for a user via one or more sensors operatively coupled with one or more personal daily oral care devices as the user is performing a periodic oral care activity with the one or more personal daily oral care devices. Collected data are subjected to cognitive diagnostics to identify abnormalities in a user's oral healthcare regimen and physiological abnormalities within the oral cavity by, for example, categorizing data over time. A report for a medical professional may be generated providing recommendations of potential diagnoses and treatment options.

One non-limiting aspect of the present invention provides a computer-implemented method for cognitive oral health management of a user comprising: collecting data for the user from at least one internet of things (IoT) sensor operatively coupled with at least one personal daily oral care device as the user is performing a periodic oral care activity with the personal daily oral care device; collecting visual image data of the oral cavity for the user from at least one visual image sensor operatively coupled with the at least one personal daily oral care device as the user is performing the periodic oral care activity with the personal daily oral care device; identifying care abnormalities in the user's oral healthcare regimen by categorizing and analyzing IoT sensor data; identifying physiological abnormalities within the oral cavity by categorizing and analyzing the visual image data; performing cognitive diagnostics over time on the identified abnormalities in the user's oral healthcare regimen and the identified physiological abnormalities within the oral cavity; and generating an oral health management report, based on the performing cognitive diagnostics, to a medical professional, the report containing recommendations of potential diagnoses and treatment options for oral health management of the user.

Another non-limiting aspect of the present invention is directed to a cognitive oral health management system for a user comprising: at least one personal daily oral care device, at least one internet of things (IoT) sensor operatively coupled with the at least one personal daily oral care device that collects IoT data for the user as the user is performing a periodic oral care activity with the personal daily oral care device; at least one visual image sensor operatively coupled with the at least one personal daily oral care device that collects visual image data for the user as the user is performing the periodic oral care activity with the personal daily oral care device; a network adapter operatively coupled with the at least one personal oral care device that forwards IoT sensor data and visual image data to a processor for executing program instructions; a memory medium including program instructions; a bus coupled to the memory medium; and the processor for executing the program instructions, the instructions causing the system to: identify care abnormalities in the user's oral healthcare regimen by categorizing and analyzing IoT sensor data; identify physiological abnormalities within the oral cavity by categorizing and analyzing individual frames in the visual image data recognition classifiers; perform cognitive diagnostics over time on the identified abnormalities in the user's oral healthcare regimen and the identified physiological abnormalities within the oral cavity; and generate an oral health management report based on the performing cognitive diagnostics to a medical professional, the report containing recommendations of potential diagnoses and treatment options for oral health management of the user.

Yet another non-limiting aspect of the present invention is directed to a computer program product for cognitive oral health management of a user, which may include, a computer readable storage device and program instructions stored on the computer readable storage device to: collect data for the user from at least one IoT sensor operatively coupled with at least one personal daily oral care device as the user is performing a periodic oral care activity with the personal daily oral care device; collect visual image data for the user from at least one visual image sensor operatively coupled with the at least one personal daily oral care device as the user is performing the periodic oral care activity with the personal daily oral care device; identify care abnormalities in the user's oral healthcare regimen by categorizing and analyzing IoT sensor data; identify physiological abnormalities within the oral cavity by categorizing and analyzing visual image data; perform cognitive diagnostics over time on the identified abnormalities in the user's oral healthcare regimen and the identified physiological abnormalities within the oral cavity' and send an oral health management report based on the performing cognitive diagnostics to a medical professional, the report containing recommendations of potential diagnoses and treatment options for oral health management of the user.

Yet still another non-limiting aspect of the present invention is directed to a method for cognitive oral health management of a user providing a computer infrastructure that includes at least one computer device that operates to perform the steps of the invention.

Yet still another non-limiting aspect of the present invention includes an apparatus for cognitive oral health management including at least one personal daily oral care device, at least one internet of things (IoT) sensor operatively coupled with the at least one personal daily oral care device, and at least one oral visual imaging sensor operatively coupled with the at least one personal daily oral care device. The at least one personal daily oral care device may include at least one communications device, at least one storage device, at least one power source, and/or at least one logic device.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings in which.

The drawings are not necessarily to scale. The drawings are merely representations, not intended to portray specific parameters of the invention. The drawings are intended to depict only typical embodiments of the invention, and therefore should not be considered as limiting in scope. In the drawings, like numbering represents like elements.

DETAILED DESCRIPTION

Illustrative embodiments will now be described more fully herein with reference to the accompanying drawings, in which illustrative embodiments are shown. It will be appreciated that this disclosure may be embodied in many different forms and should not be construed as limited to the illustrative embodiments set forth herein. Rather, these embodiments are provided so that this disclosure will be thorough and complete and will fully convey the scope of this disclosure to those skilled in the art.

Furthermore, the terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. Furthermore, similar elements in different figures may be assigned similar element numbers. The term "set" is intended to mean a quantity of at least one. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

Unless specifically stated otherwise, it may be appreciated that terms such as "processing," "detecting," "determining," "evaluating," "receiving," or the like, refer to the action and/or processes of a computer or computing system, or similar electronic data center device, that manipulates and/or transforms data represented as physical quantities (e.g., electronic) within the computing system's registers and/or memories into other data similarly represented as physical quantities within the computing system's memories, registers or other such information storage, transmission, or viewing devices. The embodiments are not limited in this context.

Unless specifically stated otherwise, an internet of things (IoT) sensor can include any sensor capable of providing data related to oral health and/or oral care devices, including, but not limited to: gyroscopes, accelerometers, tactile sensors, chemical sensors, consumption metrics, etc. An internet of things (IoT) sensor in this specification is not a visual image sensor.

Unless specifically stated otherwise, a personal daily oral care device can be any device related to oral health and used within the oral cavity, including, but not limited to: toothbrushes, flossers, water picks, oral irrigators, oral water jets, or any other oral device. A personal daily oral care device need not be used daily but, instead, can be available to the user for regular use from time to time, whether daily, weekly, monthly, or at varying times, such that data collected from the personal oral care device as the user is performing a periodic oral care activity with the personal daily oral care device can provide oral care information over time for the user. A personal oral care device can be a device used by the user in the user's regular oral hygiene regimen and may be contrasted with professional dental implements, to which a non-professional may not have access.

Unless specifically stated otherwise, the term "coincident" characteristics is intended to mean data characteristics among a population that are the same or fall within the same data range or data category within data analysis of the characteristics, or characteristics that occupy or correspond to the same place or position within particular data analysis. A "sensor of user consumption" is intended to mean a sensor capable of providing data on consumption metrics for a personal daily oral care device. A sensor "operatively coupled" with a personal daily oral care device may be operatively coupled with the device through permanent attachment to the device, semi-permanent or reversible attachment to the device, inclusion in the device as manufactured or structured, attachment to the device through glue or cement or other attachment composition, attachment using one or more of a fastening device (a strap, a screw, a rivet, an encircling device, a hook and loop fastener, etc.), attachment utilizing an elastic attachment device such as a rubber sleeve, or by any means of attachment, association, or coupling known in the art now or hereafter.

Within the current invention, it has been discovered that cognitive capabilities afforded by IoT in combination with analytic technologies may be directed to aiding oral healthcare professionals and consumers in proactively caring for their oral health. One aspect of the invention provides measurement and analysis of oral care technique, areas of neglect of oral healthcare, and monitoring for manifestations of oral disease using input from a variety of devices and sensors. This aspect allows dentists and other medical professionals to gain insight into the habits of a patient's home oral healthcare regimen, and allows for a customized conversation about proactive oral care (e.g., during routine checkups). This analysis (as well as aggregated oral health data) can allow for a better understanding of current oral health status and daily practices and, as such, can be beneficial in monitoring for signs of oral problems over time (and, potentially, in real time) and in alerting a user to see a dental specialist or to modify the user's current oral health regimen even without the direct physical assessment of an oral health professional or office visit. Among other things, substantial interventions can be provided before disease and oral tissue damage progresses—with potential meaningful cost savings associated therewith.

For example, it is understood in the oral health art that most toothbrush users brush two dominant quadrants of the user's mouth more successfully than the other two non-dominant quadrants of the mouth, resulting in more extensive plaque development and greater risk of periodontal disease and tooth decay (among other oral ailments) in the non-dominant quadrants of a user's mouth. Aspects of the current invention provide solutions for mitigating these recurrent kinds of problems in oral health management.

Embodiments of the present invention combine oral care devices, which users use in the normal course to perform periodic oral care activities, with sensors that monitor use of the devices and progress of oral care. Using sensory data to provide oral data over time, embodiments of the present invention are able, among other things, to identify neglected areas of oral healthcare, identify oral health ailments, predict forthcoming oral health ailments, and forecast and monitor improvement with changes in oral healthcare over time—all without being disruptive of everyday activity. The personal daily oral care devices with oral sensors described herein may be used at any and all times including, but not limited to, one or more times per day, one or more times per week, or some other time period during which periodic oral care activities may be performed by a user, and also may be used, for example, prior to or following a visit to a dentist. In addition, when data are collected and aggregated from multiple users representing a large pool of individuals, data scientists and oral healthcare providers may be able to distinguish valuable patterns giving insight into oral care and oral aliments and improving treatment plans.

Figure 1:
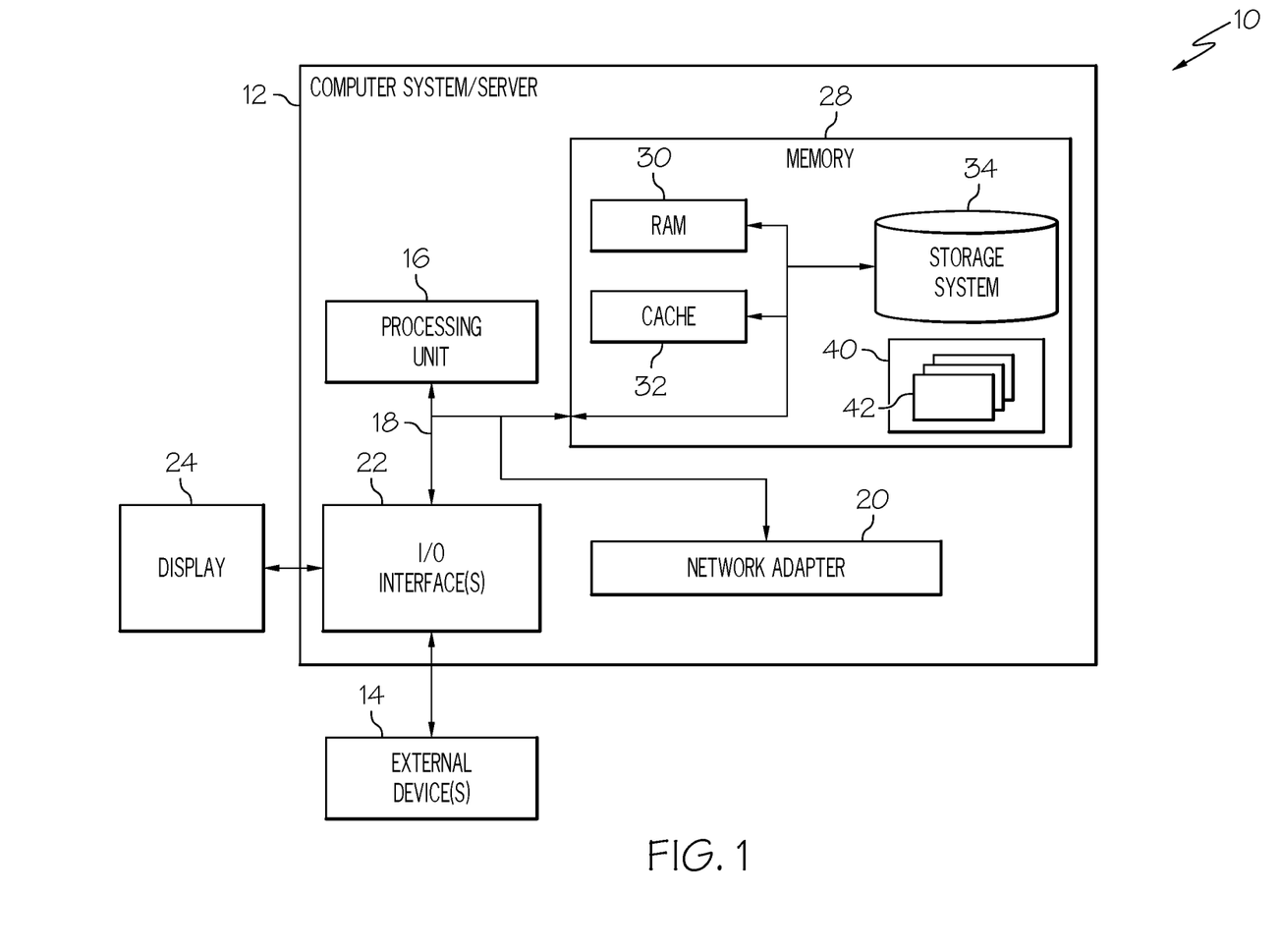
FIG. 1 shows an architecture 10 in which the present invention may be implemented according to illustrative embodiments.

Referring now to FIG. 1, a computerized implementation 10 of an embodiment for performing cognitive oral health management using IoT and visual data to provide an oral healthcare report will be shown and described. Computerized implementation 10 is only one example of a suitable implementation and is not intended to suggest any limitation as to the scope of use or functionality of embodiments of the invention described herein. Regardless, computerized implementation 10 is capable of being implemented and/or performing any of the functionality set forth hereinabove.

In computerized implementation 10, there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

This is intended to demonstrate, among other things, that the present invention could be implemented within a network environment (e.g., the Internet, a wide area network (WAN), a local area network (LAN), a virtual private network (VPN), etc.), a cloud-computing environment, a cellular network, or on a stand-alone computer system. Communication throughout the network can occur via any combination of various types of communication links. For example, the communication links can include addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer system 12 is intended to demonstrate that some or all of the components of implementation 10 could be deployed, managed, serviced, etc., by a service provider who offers to implement, deploy, and/or perform the functions of the present invention for others.

Computer system 12 is intended to represent any type of computer system that may be implemented in deploying/realizing the teachings recited herein. Computer system 12 may be described in the general context of computer system executable instructions, such as program modules, being executed by a computer system. Generally, program modules may include routines, programs, objects, components, logic, data structures, and so on, that perform particular tasks or implement particular abstract data types. In this particular example, computer system 12 represents an illustrative system for performing cognitive oral health management using IoT and visual data to provide oral healthcare diagnoses and recommendations. It should be understood that any other computers implemented under the present invention may have different components/software, but can perform similar functions. Computer system 12, as noted above in a non-limiting example, may be a server.

Computer system 12 in computerized implementation 10 is shown in the form of a general-purpose computing device. The components of computer system 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Processing unit 16 refers, generally, to any apparatus that performs logic operations, computational tasks, control functions, etc. A processor may include one or more subsystems, components, and/or other processors. A processor will typically include various logic components that operate using a clock signal to latch data, advance logic states, synchronize computations and logic operations, and/or provide other timing functions. During operation, processing unit 16 collects and routes signals representing inputs and outputs between external devices 14 and input devices (not shown). The signals can be transmitted over a LAN and/or a WAN (e.g., T1, T3, 56 kb, X.25), broadband connections (ISDN, Frame Relay, ATM), wireless links (802.11, Bluetooth®, etc.), and so on. In some embodiments, the signals may be encrypted using, for example, trusted key-pair encryption. Different systems may transmit information using different communication pathways, such as Ethernet or wireless networks, direct serial or parallel connections, USB, Firewire®, Bluetooth®, or other proprietary interfaces. (Firewire is a registered trademark of Apple Computer, Inc. Bluetooth is a registered trademark of Bluetooth Special Interest Group (SIG)).

In general, processing unit 16 executes computer program code (such as program code for performing oral diagnostics using IoT and visual data to provide an oral healthcare report), which is stored in memory 28, storage system 34, and/or program/utility 40. While executing computer program code, processing unit 16 can read and/or write data to/from memory 28, storage system 34, and program/utility 40.

Computer system 12 typically includes a variety of computer system readable media. Such media may be any available media that is accessible by computer system 12. Such media may include both volatile and non-volatile media and may include both removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media, (e.g., VCRs, DVRs, RAID arrays, USB hard drives, optical disk recorders, flash storage devices, and/or any other data processing and storage elements for storing and/or processing data). By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and/or an optical disk drive for reading from or writing to a removable, non-volatile optical disk such as a CD-ROM, DVD-ROM, or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program code embodied on a computer readable medium may be transmitted using any appropriate medium including, but not limited to, wireless, wireline, optical fiber cable, radio-frequency (RF), etc., or any suitable combination of the foregoing.

Program/utility 40, having a set (at least one) of program modules 42, may be stored in memory 28 by way of example, and not limitation. Memory 28 may also have an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a consumer to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), and/or a public network (e.g., the Internet) via network adapter 20. Communications may be undertaken through application interfaces (APIs), which can be used for detection of oral medical conditions. Measurement data that the APIs can provide include a user identity, colors, structures, certain oral chemistries, etc.

As depicted, network adapter 20 communicates with the other components of computer system/server 12 via bus 18. It should be understood that, although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
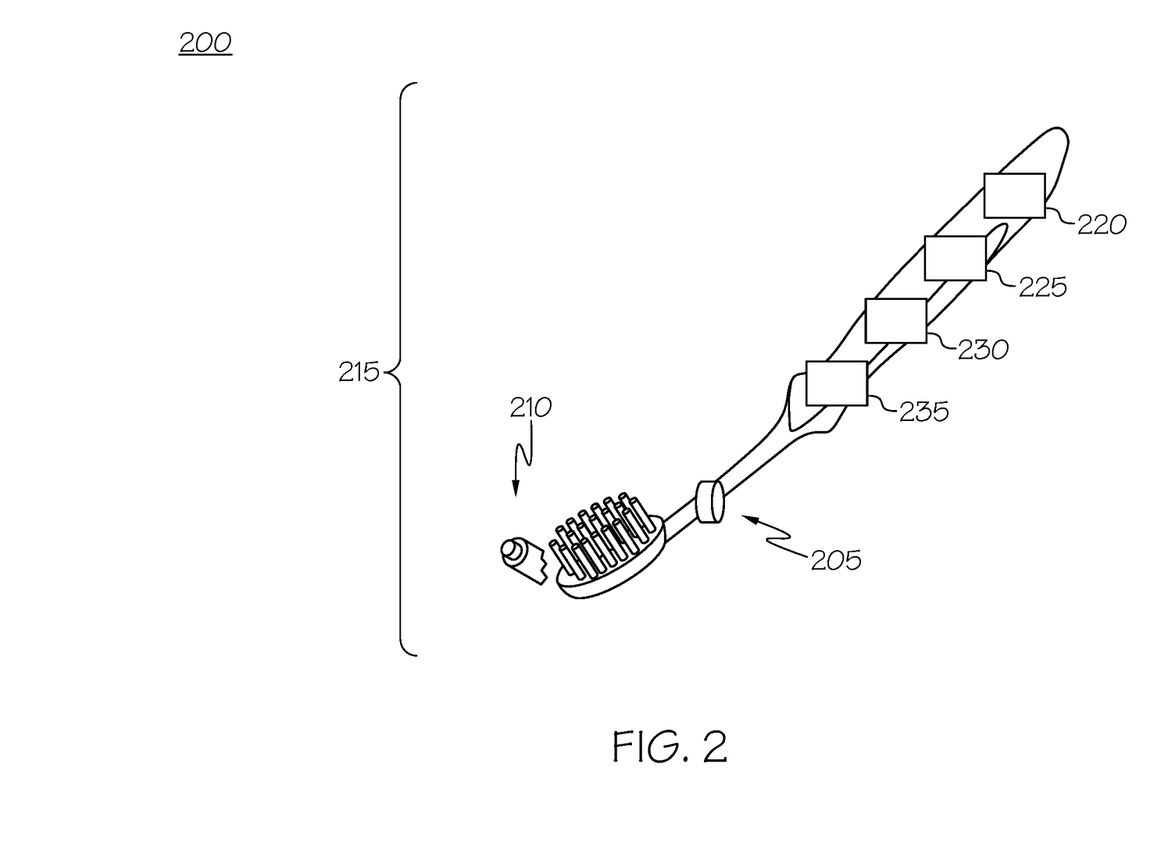
FIG. 2 shows an example of a personal daily oral care device diagram 200 with personal daily oral care device 215, operatively-coupled internet of things (IoT) oral sensor 205, and operatively-coupled oral visual imaging sensor 210 according to illustrative embodiments.

Referring now to FIG. 2, personal daily oral care device diagram 200 according to an embodiment of the present invention will be shown and described. An example personal daily oral care device 215 is shown with operatively-coupled oral IoT sensor 205 and oral visual image sensor 210. Operatively coupled power supply 220, storage component 225, communications component 230, and processor 235 are likewise shown. Within personal daily oral care device 215, IoT sensor 205 and image sensor 210 each collect data as a user employs device 215 to perform a periodic oral care activity. Device 215 can be any oral home health device including and not limited to a toothbrush, a flosser, a water pick, an oral irrigator, an oral water jet, or any other oral device, appliance, or apparatus. IoT sensor 205 may include one or more sensors which can include a timer and/or clock, a gyroscope, an accelerometer, a tactile sensor, a chemical sensor, a thermometer, a pH sensor, an ion sensor, a bacterial sensor, such as, for example, a polyaniline colorimetric sensor, an oxidation/reduction or other anaerobiosis sensor, a nutrient sensor, a sensor capable of identifying concentrations of hydrogen sulfide, methyl mercaptan, dimethyl sulfide, cadaverine, putrescine, skatole or other molecule, and/or any sensor contemplated by one of skill in the art now and hereafter. Image sensor 210 may include one or more sensors, which can include, a camera, an infrared camera, an ultraviolet camera, or any image detector capable of capturing any electromagnetic radiation source. Image sensor 210 may include a light source such as a visual light source, an infrared light source, an ultraviolet light source, a laser, or any other source of electromagnetic radiation. Image sensor 210 may identify colors, structures, patterns, etc. Sensor data may be collected and sent over a network (e.g., via communications component 230) to be stored and processed. Either or both of IoT sensor 205 or image sensor 210 may be connected to an amplifier to amplify the external signal of the sensor. Additionally or in the alternative, either or both of IoT sensor 205 or image sensor 210 may be biology enabled.

Using data that has been aggregated over time, analysis can be conducted of oral hygiene techniques to manifest regions being chronically neglected during daily hygiene and/or chemical data may be collected to identify neglected areas or areas in need of medical attention. Additionally, collected visual image data may be analyzed over time and progression or regression of identified anomalies may be identified. Oral chemistry data may likewise be collected to identify changes in oral health over time. Generally, an individual's classifier for any of these data becomes more accurate over time using advanced augmented intelligence techniques such as machine learning, which may identify anomalies unique to each individual's mouth.

IoT sensor 205 and image sensor 210 can be operatively coupled with oral device 215 by any method known in the art now and hereafter. IoT sensor 205 and image sensor 210 can be housed within the structure of oral device 215, such as within the plastic structure of a toothbrush, flosser, oral irrigator, etc. Sensor 205 and 210 may, for example, be attached to oral device 215 via an elastic sleeve around oral device 215. Image sensor 210 can be affixed, for example, in the portion of oral device 215 that is placed within the oral cavity, such as, for example, on the head of a toothbrush. IoT sensor 205 and image sensor 210 can each include a power source or may share a power source or may share power source 220 with oral device 215. IoT sensor 205 and image sensor 210 can individually internally contain components with the capacity to store and/or transmit data over a network protocol or may share these components with oral device 215.

Communications component 230 can be any communications device known in the art now and hereafter including, for example, any combination of wired and/or wireless transmission methods such as those described for I/O interfaces 22. Capacity of IoT sensor 205 and image sensor 210 to transmit data through communications component 230 continually over a network protocol, when available, may allow computer system 12 to undergo real-time analysis of the provided data. Storage component 225 can be any storage device known in the art now and hereafter including, for example, storage devices described for storage system 34. Storage capacity, for example, provides the ability to continue collecting oral health data even when not connected to an external storage system through a wireless or other network connection. Power source 220 can be any power source known to one of skill in the art now and hereafter, including, for example, a 120 or 240 volt plug, a battery, a capacitor, an ultrasonic generator, an inductive coupling generator, a thermoelectric generator, any biology-enabled generator, etc. Processor 235, generally, can be any apparatus that performs logic operations, computational tasks, control functions, etc., as described, for example, for processor 16. In a non-limiting embodiment, oral monitoring device 205 may contain processor 16 within computer system 12.

IoT sensor 205 and image sensor 210 can include groups of sensors used for collecting and processing data. Sensors may be of any size capable of being included within or attached to oral device 215. In a typical embodiment, IoT sensor 205 and image sensor 210 are sufficiently small not to interfere with an individual's use of oral device 215. Oral device 215 may include, as a non-limiting example, any microdevice currently or hereinafter known as useful in a mobile telephone. Together, IoT sensor 205 and image sensor 210 (or pluralities thereof), may, for example, allow recording of the position of oral device 215 in the oral cavity at all times when oral device 215 is in use.

In a non-limiting embodiment, sensor data may be used to track at-home oral care and may be used to track anomalies/ abnormalities of oral health including both progression of anomalies and severity of anomalies. The collected data may be included within a larger data set encompassing other facets of oral healthcare. Collection of these data over time may provide robust long-term temporal data capture, enabling an accurate classifier to be constructed for each individual, as well as greater crowdsourcing of data. These data may then be collected and sent to a dental professional and/or a data scientist for appropriate actions.

Another non-limiting aspect of the invention provides modifications to a personal daily oral care (e.g., home dental) device to create oral device 215 by affixing or otherwise operatively coupling IoT sensor 205 and image sensor 210 to device 215 for performing embodiments of the invention.

Figure 3:
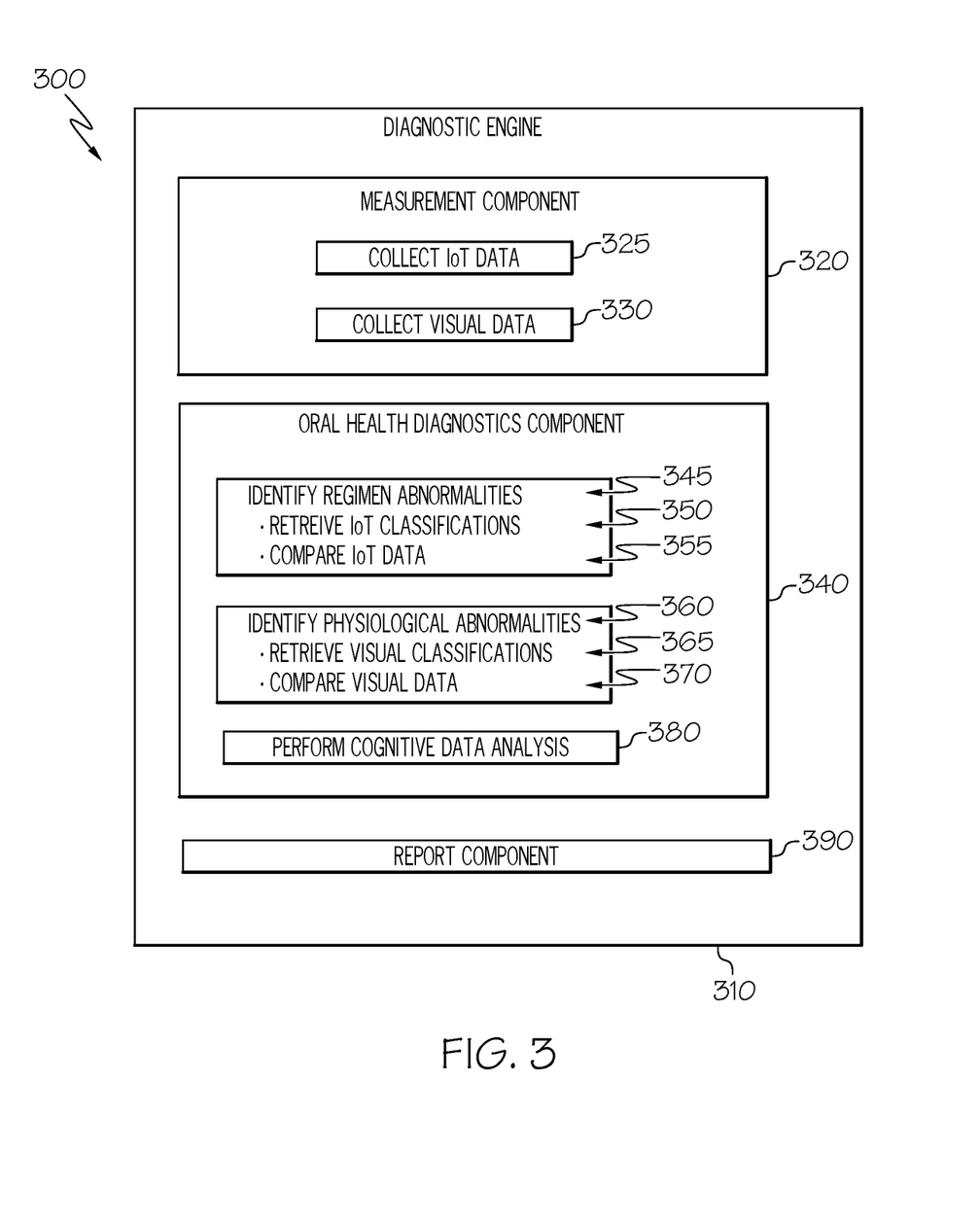
FIG. 3 shows a block diagram 300 that illustrates a system according to illustrative embodiments.

Referring now to FIG. 3, a block diagram 300 describing the functionality discussed herein according to an embodiment of the present invention is shown. It is understood that the teachings recited herein may be practiced within any type of computing environment (e.g., computer system 12). To this extent, the teachings recited herein may be practiced within a stand-alone computer system or within a networked computing environment (e.g., a client-server environment, peer-to-peer environment, distributed computing environment, cloud computing environment, and/or the like). If the teachings recited herein are practiced within a networked computing environment, each physical server need not have a diagnostics engine (hereinafter "system 310"). Rather, system 310 could be loaded on a server or server-capable device that communicates (e.g., wirelessly) with the physical server. Regardless, as depicted, system 310 can be implemented as program/utility 40 on computer system 12 and can enable the functions recited herein. It is further understood that system 310 may be incorporated within or work in conjunction with any type of system that receives, processes, and/or executes commands with respect to information technology (IT) resources in a networked computing environment. Such other system(s) have not been shown in FIG. 3 for brevity purposes.

Figure 4:
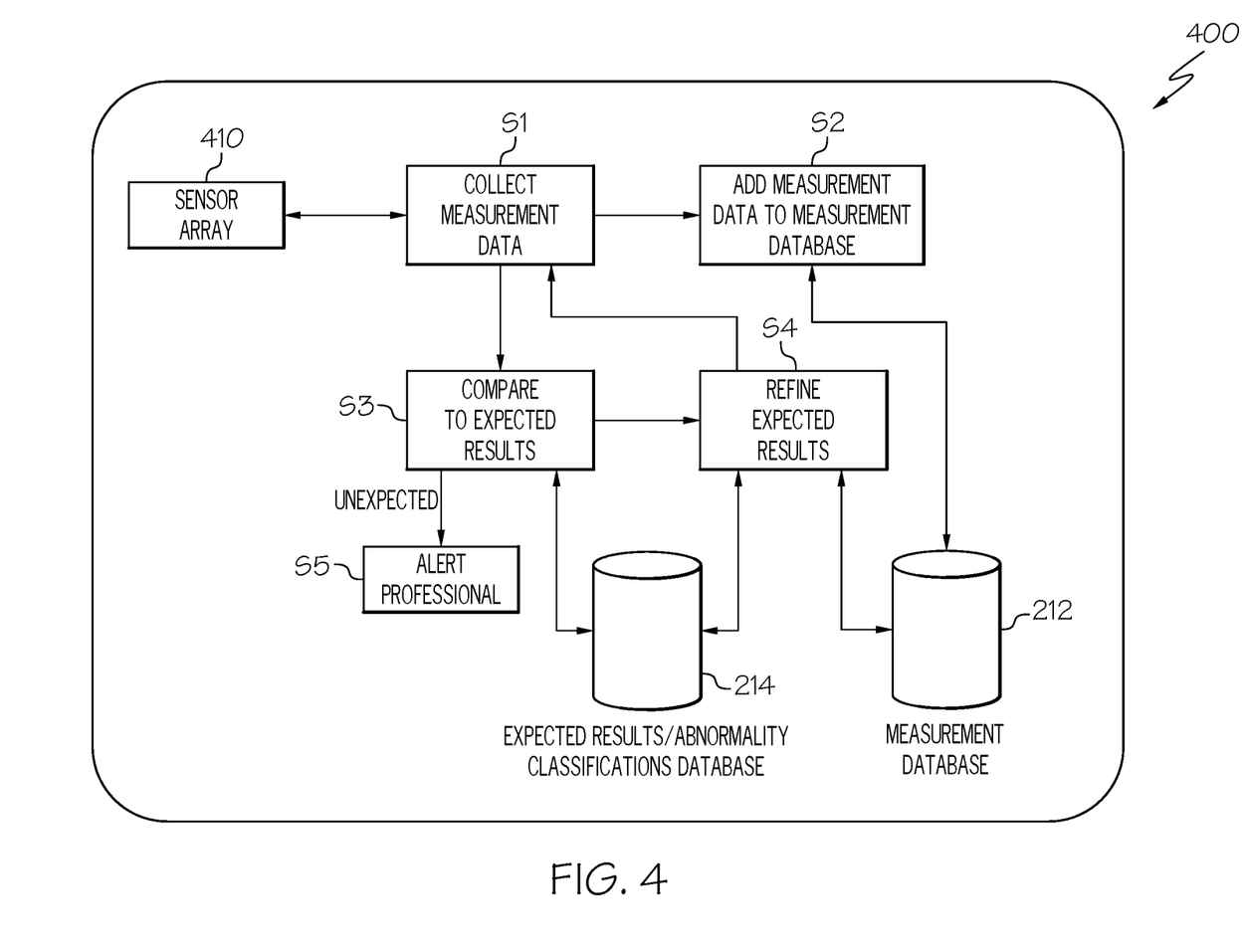
FIG. 4 shows a flow diagram 400 for performing an oral health diagnosis using an oral IoT sensor and an oral visual sensor to generate an oral healthcare report according to illustrative embodiments.

Referring now to FIG. 4 in conjunction with FIGS. 1-3, an example flow diagram 400 for performing cognitive oral health management according to an embodiment of the invention is shown. At S1, IoT sensor 205 and image sensor 210, together as sensor array 410, collect measurement data as a user uses personal daily oral device 215 (e.g., as the user is performing a periodic oral care activity with the personal daily oral care device). Measurement component 320 of system 310, as executed by computer system/server 12, is configured to receive any collected measurement IoT data at collect IoT data 325 and visual data at collect visual data 330. For example, sensor array 410 may be designed to transmit data measurements to measurement component 320 via data transmission. Data transmission may be performed, either by wire or wirelessly, in accordance with appropriate transmission principles known in the art, and data encryption may be employed, if desired. Measurement data may be periodically received by measurement component 320 (e.g., as user employs oral device 215), or may be pushed to measurement component 320 (e.g., nightly), or may be pulled to measurement component 320 (e.g., periodically, dynamically, randomly), or so forth. At S2, measurement data may be accumulated over a period of time and stored in measurement database 212 in order to accumulate quantitative oral health diagnostic data to derive an oral health diagnostic (at oral health diagnostic component 340) of a particular user.

Oral health diagnostic component 340 of system 310, as executed by computer system/server 12, is configured to analyze measurement data collected by measurement component 320 to transform raw measurement data into oral healthcare diagnostics by identifying trends, patterns, and deviations in the data.

To assess a user's use of oral device 215 and user's resulting oral health over time, at S3, current measurement data acquired by measurement component 320 and expected results classifications or abnormality classifications stored in expected results/abnormality classifications database 214 are made accessible to oral health diagnostics component 340 to retrieve IoT abnormality classifications (or expected results) 350 and visual abnormality classifications (or expected results) 365. Oral health diagnostics component 340 may compare collected IoT data 325 to retrieved IoT abnormality classifications (or expected results) 350 at compare IoT data 355 and may compare collected visual data 370 to retrieved visual abnormality classifications (or expected results) 365 to identify regimen abnormalities 345 of the user and to identify physiological abnormalities 360 of the user if the comparison identifies a deviation exceeding a predefined permissible threshold of expected results or falling within an abnormality classification. Expected results and abnormality classifications may be derived from a user's historical measurement data, historical measurements of other individuals, medical studies, medical trials, medical research, medical professionals, and/or data scientists, among others. Expected results can be used to provide an acceptable oral health image profile range for a particular user. Abnormality classifications may be used to identify unacceptable visual image patterns (such as, for example, plaque on specific teeth, gingivitis, gum irritation, dental caries, bacterial growth, erosion lesions, tartar, disease of hard or soft tissues, presence of chemical signals (such as signals of putrification, bad breath, etc.), tissue damage, cancerous tissue, tooth reduction, etc.).

For example, a user may have a pattern of color in the mouth that is different from a baseline pattern. When a deviation of the color pattern of the user's mouth exceeds a permissible threshold as compared to expected results (or falls within an abnormality classification), this may indicate a need for medical intervention. Advanced image recognition classifiers, such as those offered by Watson® Visual Recognition™ (a trademark of International Business Machines Corporation of Armonk, N.Y., in the United States and/or other jurisdictions), may categorize the individual frames to determine gum health, mouth sores, cancer, and other anomalies within the oral cavity. Data from individual users may be aggregated to create crowd-sourced data. These data may be classified with specific use cases enabling the creation and development of a medical corpus of oral-related data. A corpus of medical oral data utilizing crowd-sourcing may allow for data categorization across populations.

As more and more data points are collected for an individual, machine learning techniques may refine cognitive classifiers to statistically identify when the individual has data points that are within abnormality classifications or outside of the norm of expected results. Statistical analysis may be employed to identify statistically significant abnormalities in use of personal daily oral care devices or oral health or both. Acquisition of non-personal (sanitized) data for aggregate analysis and trending information may be used for analysis based on crowd sources. In one non-limiting embodiment, analysis of the crowd-sourced data would employ a normal Gaussian distribution to derive a continuous probability distribution model across a population. Through Gaussian distribution models, outliers within an abnormality classification or outside an expected result are identified within the distribution model. In another embodiment, once outliers are properly identified, a medical professional is informed of the outlying data and can take proper action based upon the diagnostics of the data collected.

If a deviation exceeding a permissible threshold from expected results is not detected, current measurement data are accumulated with expected results from expected results database 214 at S4 to refine expected results or abnormality classifications, further contributing to the derivation of the oral health data of the user being monitored as well as data of an aggregated similar population with coincident data characteristics. The accumulation of measurement data stored at S2 is linked back to S4 to allow for ongoing comparison of incoming measurement data with previously accumulated expected results or abnormality classifications. Further, database 214 may continually be refined by historical measurements of other individuals, medical trials and/or research, medical professionals, and data scientists, among others. Analyzed data may include images, IoT data, manual inputs, etc.

In a non-limiting embodiment, data collected from an individual and across a population is analyzed employing cognitive data analysis 380. Recommendations based on existing data may be derived through the effective use of cognitive tradeoff analytics. Utilizing all data patterns for cause and effect analysis of the existing known oral health data, medical journals, and historical crowd-sourced data, an approach for recommending treatment options may be derived based on best case scenarios for patients with coincident oral health and oral health practices. Within machine learning, an application is provided additional data and trained over time to produce quality results for medical recommendation usage. Cognitive tradeoff analytics may be accomplished through an application-programming interface such as Watson® Tradeoff Analytics API™ (a service mark of International Business Machines Corporation of Armonk, N.Y., in the United States and/or other jurisdictions).

For cognitive diagnostics and machine learning, methods of identifying physiological anomalies within the oral cavity by categorizing individual frames in the visual image data using image recognition classifiers may be learned by the system. Likewise methods of identifying areas of neglect of oral healthcare regimens or anomalies in oral healthcare regimens based on spatial and temporal or chemical analysis of the IoT sensor data as a function of time may be learned by the system.

Regarding oral medical imaging automation and spatio-temporal neglect analysis, detection of certain abnormal visual anatomy classifiers and certain spatio-temporal pattern classifiers can be learned by the system. In general, a large number of abnormal and normal examples are labeled by an expert. A classifying score may be assigned to each individual frame in visual image data for machine learning in oral imaging or each spatio-temporal data set in the oral healthcare regimen for machine learning in identifying areas of neglect. An image set or spatio-temporal set having a higher score may be labeled as abnormal, while an image set having a lower score may be labeled as normal (otherwise an expected result). Further input from oral healthcare professionals allows refinement of the scoring system. Extensive data and training over time allows the system to better recognize anomalies and provide higher quality medical recommendations.

Report component 390 of system 310, as executed by computer system/server 12, is configured to perform a report procedure when a deviation exceeding a permissible threshold is determined by health diagnostics component 340, at S5. For example, a modified personal daily oral care device may detect development of plaque on certain teeth of a user correlated with the user's limited use of the device in certain parts of the mouth. Use of the device on certain teeth may fall below a predefined threshold (e.g., five percent below threshold) and may indicate a need for increased brushing. Notification producers executed at S5 may include transmission of an alert notification (e.g., email message, text message, etc.) as report component 390 to a caregiver (e.g., oral healthcare professional, doctor, etc.) and/or to the user. The individual is alerted of the identified neglect and resulting plaque development through report component 390. The individual's medical professional is alerted of the identified neglect and the identified development of plaque on specific teeth through report component 390.

Figure 5:
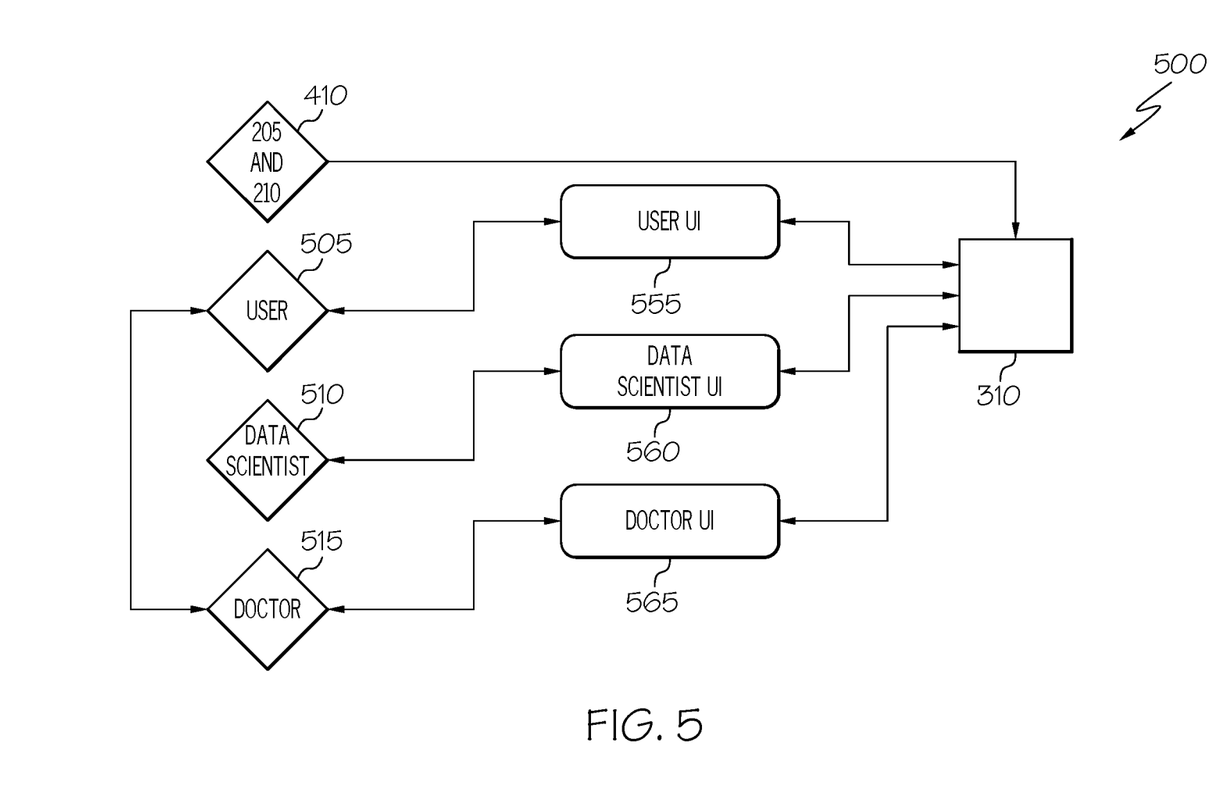
FIG. 5 shows a block diagram 500 describing the user interface functionality for displaying an oral healthcare report according to illustrative embodiments.

FIG. 5 shows a block diagram 500 describing the user interface functionality for generating a cognitive oral health management report according to an embodiment of the present invention. As shown, block diagram 500 includes sensor array 410 (combining at least IoT sensor 205 and image sensor 210), system 310, user 505 having an electronic device with user interface (UI) 555, data scientist 510 having an electronic device with data scientist UI 560, and oral healthcare doctor (such as a dentist, hygienist, or maxillofacial surgeon) 515 having an electronic device with doctor UI 565. A suitable electronic device for communicating with system 310 may include, but is not limited to, a smart phone, a tablet computer, a laptop, and/or a desktop computer.

In a non-limiting embodiment, using user UI 555, user 505 can view the user's historical oral measurement data, any trends or patterns derived from the user's historical oral measurement data, and/or any feedback provided by an oral healthcare professional (e.g., doctor 515) based on the user's collected measurement data and expected results (e.g., improved gum health, reduced rate of tooth loss from bruxism, etc.). Using doctor UI 565, doctor 515 (or other oral healthcare professional) can view a user's historical measurement data. Based on the user's historical measurement data, doctor 515 can determine any user trends or patterns (e.g., gum line recession, plaque development, possible cancerous growths, etc.), identify any potential oral health causes based on user patterns (e.g., reduction in flossing, reduction in brushing, increased consumption of sugar, increased dry mouth, etc.) and provide any feedback to user 505 (e.g., schedule a dental appointment, etc.). Further, doctor 515 can consider any potential health causes based on trends across multiple users employing sanitized collected historical measurement data. Using data scientist UI 560, data scientist 510 can view measurement data of user 505 and/or others, perform any data cleansing (e.g., to be viewed by user 505 and/or doctor 515), and/or analyze historical measurement data to identify any trends or patterns across users.

As discussed, system 310 may perform an oral health diagnosis by comparing measurement data of a user to expected results or to abnormality classifications. For example, Alya uses a modified personal daily oral device 215 (e.g. toothbrush) having an IoT oral sensor 205 (e.g. gyroscope) and oral visual image sensor 210 (e.g., camera with light source) that allows the capture of data concerning what sections of Alya's mouth are receiving brushing time. Alya is provided software for program module 42 on her smart phone acting as computer system 12 that allows communication with IoT sensor 205 and image sensor 210. Data from IoT sensor 205 and image sensor 210 are recorded and stored in storage system 34.

The collected data are received by measurement component 320. Oral health diagnostics component 340 compares the current measurement data with expected results and/or abnormality classifications. Over time, the camera captures the development of plaque on the teeth of the back lower right quadrant of Alya's mouth. Oral health diagnostics component 340 shows that Alya is spending insufficient time brushing those teeth. Based on the comparison and historical measurement data of others, doctor 515 is notified through report component 390 and identifies the trend of neglected teeth. Doctor 515 recommends Alya increase brushing of specific areas of the mouth. Once Alya is notified of the trend and receives recommendations from doctor 515, measurement data are further collected from IoT oral sensor 205 and image sensor 210 so that doctor 515 can determine how well the increased brushing regimen is working for Alya. The collected measurement data can be used to create personalized treatment plans for Alya and, potentially, for one or more other similarly-situated users with coincident data characteristics.

In another example, Alejandro uses a modified personal daily oral care device 215 (e.g., oral irrigator) having an IoT sensor 205 (e.g., accelerometer) and image sensor 210 (e.g., camera with light source). The modified oral irrigator tracks what areas of the mouth receive attention. Measurement data are received by measurement component 320. Oral health diagnostics component 340 compares the current measurement data with expected results and/or abnormality classifications and combines the current measurement data with pocket-depth tracking from a hygienist. Oral health diagnostics component 340 recognizes that identified periodontal pockets are becoming inflamed in an area of the mouth that is already at risk. Based on the analysis and historical measurement data of others from report component 390, doctor of dental medicine 515 notices that Alejandro is not focusing on using the oral irrigator between two specific teeth. Doctor 515 recommends Alejandro provide more oral health maintenance time between the two neglected teeth.

In yet another example, Alejandro's personal daily oral care device 215 (e.g., oral irrigator) has an additional IoT sensor 205 (pH meter). IoT sensor 205 detects a lowering of pH in Alejandro's mouth as image sensor 210 detects an increase in bacterial growth. Measurement data are received by measurement component 320. Oral health diagnostics component 340 compares the current measurement data with expected results and/or abnormality classifications and recognizes that Alejandro's oral hygiene is not sufficiently controlling bacterial growth. Report component 390 generates a report suggesting increased oral hygiene care.

In another example, image sensor 210 (e.g., camera) on oral device 215 (e.g. a flosser) captures changes in growth inside the cheek of user Mary and IoT sensor 205 (e.g., lactate detector, pH meter, etc.) detects increase in lactate in extracellular environment. Measurement data are received by measurement component 320. Oral health diagnostics component 340 compares the current measurement data with expected results. When compared to database images and pH measurements, the system identifies that oral cancer risk is present. The system notifies Mary's doctor 515 and suggests the doctor contact Mary to request an appointment.

Figure 6:
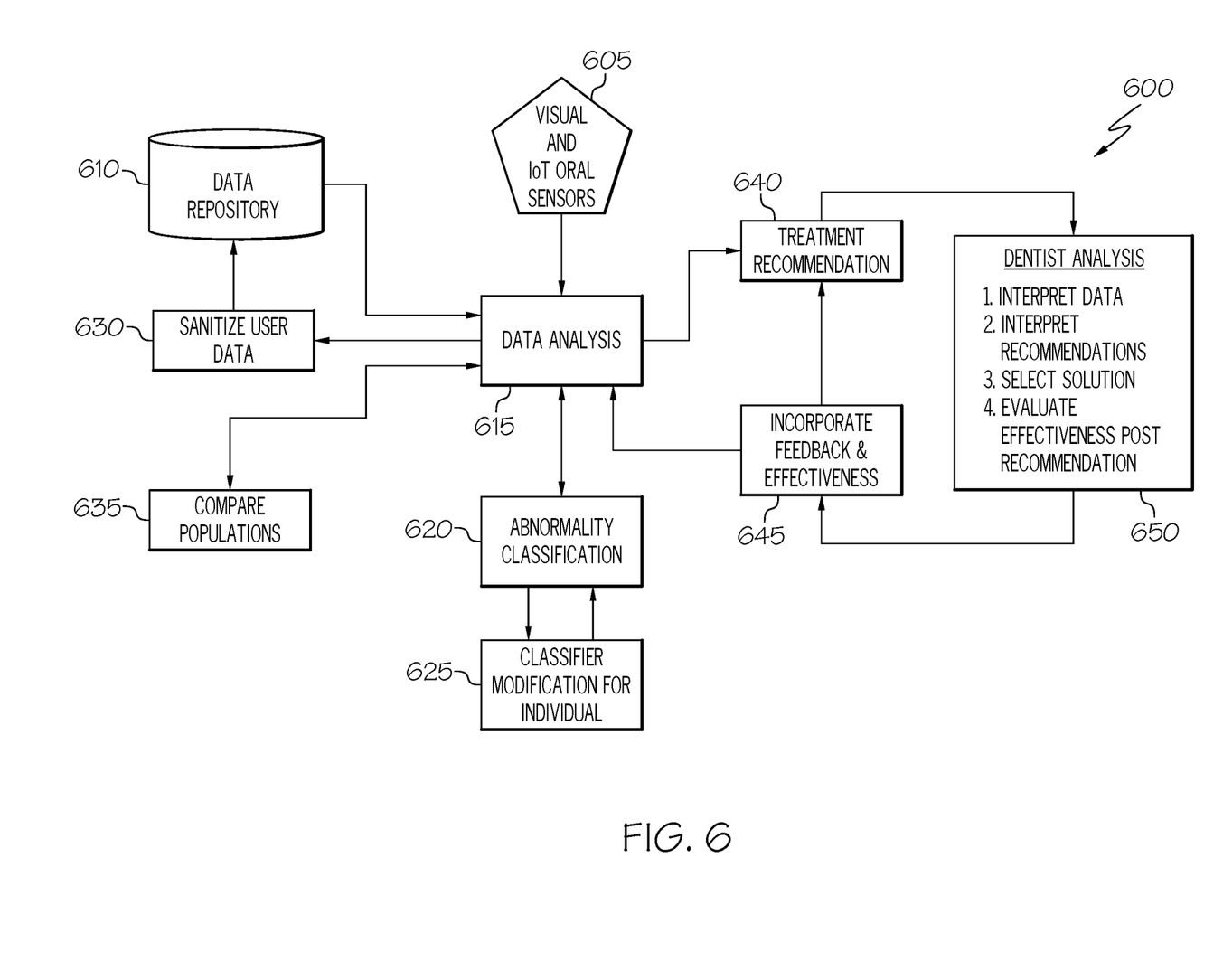
FIG. 6 shows a flow diagram 600 for performing an oral health diagnosis using oral sensors to generate a treatment recommendation report to an oral healthcare professional according to illustrative embodiments.

Referring now to FIG. 6 in conjunction with FIGS. 1-3, an example flow diagram 600 for cognitive oral health management according to an embodiment of the invention is shown. Oral IoT sensor 205 and oral visual image sensor 210 (together with Visual and IoT Oral Sensors 605) operatively-coupled with oral device 215 collect data as device 215 is used in daily life.

Measurement component 320 of system 310, as executed by computer system/server 12, is configured to receive any measurement data collected by visual and IoT oral sensors 605 at collect IoT data 325 and collect visual data 330. Within diagnostics engine 310, the data pushed or pulled to measurement component 320 are analyzed in data analysis 615. Oral sensor data in data analysis 615 are analyzed by comparison against abnormality classification 620 at oral health diagnostics component 340 including identify regimen abnormalities 345 through retrieve IoT classifications 350 and compare IoT data 355 and identify physiological abnormalities 360 through retrieve visual classifications 365 and compare visual data 370. Data are cognitively analyzed at perform cognitive data analysis 380 as employed in data analysis 615. Oral sensor data in data analysis 615 may be cognitively compared to at least one similarly-situated population with coincident data characteristics in compare populations 635 by drawing data from data repository 610. Abnormality classification 620 is further modified for the individual data from visual and IoT oral sensors 605 in classifier modification for individual 625.

Data from visual and IoT oral sensors 605 analyzed in data analysis 615 are subject to removal of personal identifying information at sanitize user data 630 and submitted to data repository 610 for inclusion in aggregated oral health data in data repository 610. Aggregated data from data repository 610 are included in data analysis 615. Data analysis 615 provides a treatment recommendation 640, which may be, for example, a report to an oral health professional, such as a dentist, from report component 390. The oral health professional provides dentist analysis 650 including interpreting data, interpreting recommendations provided at treatment recommendation 640, selecting solution, and evaluating effectiveness of solution post recommendation. Dentist analysis 650 is incorporated into treatment recommendation 640 through incorporate feedback and effectiveness 645. Incorporated feedback and effectiveness 645 is included in data analysis 615 which is sanitized via sanitize user data 630 and included in data repository 610.

Treatment recommendation 640 may be included in a report to an oral health professional through report component 390. Reporting to an oral health professional and/or to a user may be accomplished by any method known now or hereafter in the art. Non-limiting examples of reporting mechanisms include email, SMS text, letter, aural notification (including, for example, voice notification or sound notification), pager notification, visual notification (such as, for example, a blinking light), or any other notification. Reporting may be at regular intervals or any other interval or may be, for example, only when an anomaly or abnormality is identified by the system.

As a non-limiting example, Jose has teeth missing at positions 5, 20, and 30. Jose has a bridge for his lower missing teeth at positions 20 and 30. For one week before his bi-annual cleaning, Jose is given a personal daily oral care device 215 with operatively-coupled IoT sensor 205 and image sensor 210 (together 605). Oral health data retrieved from the oral sensor at the bi-annual cleaning reveal an image pattern cognitively associated through data analysis 615 as compared to abnormality classification 620 with periodontal disease progressing because of neglect of areas around missing teeth. Data analysis 615 includes information concerning Jose's missing teeth and use of bridge. Data analysis 615 compares Jose's data to sanitized user data 630 in data repository 610. Data analysis correlates Jose's jaw structure, missing teeth, use of bridge, height, weight, gender, age, brushing time, flossing time, etc., with a similarly-situated population with coincident data characteristics at compare populations 635 and cognitively devises a treatment recommendation within a 95% confidence interval, weighted by effectiveness, based on treatments and success with similar abnormalities in the similarly-situated population. Jose's dentist is notified at report component 390 and a treatment recommendation is provided to construct a newly-designed bridge along with increased oral hygiene time with particular focus on areas around missing teeth. Jose's dentist analyzes the data, interprets the recommendation, selects a solution, and monitors post effectiveness by maintaining use of oral device 215 with operatively-coupled visual and IoT oral sensors 605. The new feedback and effectiveness data are incorporated in data analysis 615, sanitized at sanitize user data 630, and entered into data repository 610.

As an example, Katy receives braces. IoT sensor 205 (gyroscope) and image sensor 210 (camera and light source) on oral device 215 (irrigator) capture data suggesting that tooth movement has stopped and braces need to be adjusted. After the braces are removed, gyroscope 205 and camera 210 capture data suggesting that some teeth are moving back to their original problem positions. The system analyzes the received data and determines Katy is not wearing her retainer over sufficient time periods. A report (390) to Katy and her oral healthcare provider suggests Katy wear a retainer a specific number of hours per day. An improved retainer is recommended.

Referring back to FIG. 4 and FIG. 6, process flowcharts 400 and 600 illustrate the architecture, functionality, and operation of possible implementations of systems, methods, and computer program products according to various embodiments of the present invention. In this regard, each block in the flowchart may represent a module, segment, or portion of code, which includes one or more executable instructions for implementing the specified logical function (s). It should also be noted that, in some alternative implementations, the functions noted in the blocks might occur out of the order depicted in the figures. For example, two blocks shown in succession may, in fact, be executed substantially concurrently. It will also be noted that each block of flowchart illustrations can be implemented by special purpose hardware-based systems that perform the specified functions or acts, or combinations of special purpose hardware and computer instructions.

Some of the functional components described in this specification have been labeled as systems or units in order to more particularly emphasize their implementation independence. For example, a system or unit may be implemented as a hardware circuit including custom VLSI circuits or gate arrays, off-the-shelf semiconductors such as logic chips, transistors, or other discrete components. A system or unit may also be implemented in programmable hardware devices such as field programmable gate arrays, programmable array logic, programmable logic devices or the like. A system or unit may also be implemented in software for execution by various types of processors. A system or unit or component of executable code may, for instance, include one or more physical or logical blocks of computer instructions, which may, for instance, be organized as an object, procedure, or function. Nevertheless, the executables of an identified system or unit need not be physically located together, but may include disparate instructions stored in different locations which, when joined logically together, include the system or unit and achieve the stated purpose for the system or unit.

Further, a system or unit of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices and disparate memory devices.

Furthermore, systems/units may also be implemented as a combination of software and one or more hardware devices. For instance, program/utility 40 may be embodied in the combination of a software executable code stored on a memory medium (e.g., memory storage device). In a further example, a system or unit may be the combination of a processor that operates on a set of operational data.

As noted above, some of the embodiments may be embodied in hardware. The hardware may be referenced as a hardware element. In general, a hardware element may refer to any hardware structures arranged to perform certain operations. In one embodiment, for example, the hardware elements may include any analog or digital electrical or electronic elements fabricated on a substrate. The fabrication may be performed using silicon-based integrated circuit (IC) techniques, such as complementary metal oxide semiconductor (CMOS), bipolar, and bipolar CMOS (BiCMOS) techniques, for example. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor devices, chips, microchips, chip sets, and so forth. However, the embodiments are not limited in this context.

Any of the components provided herein can be deployed, managed, serviced, etc., by a service provider that offers to deploy or integrate computing infrastructure with respect to a process for performing cognitive oral health management. Thus, embodiments herein disclose a process for supporting computer infrastructure, comprising integrating, hosting, maintaining, and deploying computer-readable code into a computing system (e.g., computer system 12), wherein the code in combination with the computing system is capable of performing the functions described herein.

In another embodiment, the invention provides a method that performs the process steps of the invention on a subscription, advertising, and/or fee basis. That is, a service provider, such as a Solution Integrator, can offer to create, maintain, support, etc., a process for performing oral diagnostics using IoT data and visual data to provide an oral healthcare report. In this case, the service provider can create, maintain, support, etc., a computer infrastructure that performs the process steps of the invention for one or more customers. In return, the service provider can receive payment from the customer(s) under a subscription and/or fee agreement, and/or the service provider can receive payment from the sale of advertising content to one or more third parties.

Also noted above, some embodiments may be embodied in software. The software may be referenced as a software element. In general, a software element may refer to any software structures arranged to perform certain operations. In one embodiment, for example, the software elements may include program instructions and/or data adapted for execution by a hardware element, such as a processor. Program instructions may include an organized list of commands including words, values, or symbols arranged in a predetermined syntax that, when executed, may cause a processor to perform a corresponding set of operations.

The present invention may also be a computer program product. The computer program product may include a computer readable storage medium (or media) having computer readable program instructions thereon for causing a processor to carry out aspects of the present invention. The computer readable storage medium can be a tangible device that retains and stores instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture such as, for example, instructions that implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

It is apparent that there has been provided herein approaches for performing cognitive oral health management using data from an oral device operatively coupled with at least one oral IoT sensor and at least one oral visual image sensor. While the invention has been particularly shown and described in conjunction with exemplary embodiments, it will be appreciated that variations and modifications will occur to those skilled in the art. Therefore, it is to be understood that the appended claims are intended to cover all such modifications and changes that fall within the true spirit of the invention.

What is claimed is:

1. A computer-implemented method for cognitive oral health management of a user comprising:

collecting data for the user from at least one Internet of things (IoT) sensor operatively coupled with at least one personal daily oral care device as the user is performing a periodic oral care activity with the personal daily oral care device;

collecting visual image data of the oral cavity for the user from at least one visual image sensor operatively coupled over an encrypted connection with the at least one personal daily oral care device as the user is performing the periodic oral care activity with the personal daily oral care device;

identifying care abnormalities in an oral healthcare regimen of the user by categorizing and analyzing IoT sensor data;

identifying physiological abnormalities within the oral cavity by categorizing and analyzing the visual image data;

performing real-time analysis and cognitive diagnostics over time via a cognitive engine using machine learning augmented intelligence techniques and cognitive data analysis that implements cognitive tradeoff analytics on the identified abnormalities in the oral healthcare regimen of the user and the identified physiological abnormalities within the oral cavity based on crowdsourced data; and, generating an oral health management report based on the performing cognitive diagnostics to a medical professional, the report containing recommendations of potential diagnoses and treatment options for oral health management of the user, wherein said identifying care abnormalities in the oral healthcare regimen of the user further comprises categorizing and analyzing at least one of spatial, temporal, and chemical data collected from the IoT sensor, wherein said identifying physiological abnormalities within the oral cavity further comprises categorizing and analyzing individual frames in the visual image data using cognitive visual recognition engine-based image recognition classifiers and classifying resulting data with specific use cases to create and develop a medical corpus of oral-related data utilizing crowdsourcing, and wherein the instructions causing the system to perform real-time analysis and cognitive diagnostics over time further comprise analyzing a combination of the visual image data and spacio-temporal and chemical analysis data within the sensor data to correlate an identified physiological anomaly with an identified neglect in the oral healthcare regimen of the user.

2. The computer-implemented method of claim 1, wherein the identifying of the care abnormalities in the oral healthcare regimen of the user further comprises:

retrieving a set of abnormality classifications for the at least one IoT sensor from a database; and comparing the data for the user from the at least one IoT sensor to the set of abnormality classifications for the IoT sensor data, and wherein the identifying of the physiological abnormalities within the oral cavity further comprises:

retrieving a set of abnormality classifications for the at least one visual image sensor from a database; and comparing the visual image data for the user to the set of abnormality classifications for the visual image data.

3. The computer-implemented method of claim 1, wherein the performing of the cognitive diagnostics over time further comprises comparing user data with a crowdsourcing baseline containing data from a population with coincident characteristics based on expected results and abnormality classifications derived from historical measurement data of the user, historical measurements of other individuals, medical studies, medical trials, medical research, medical professionals, and data scientists.

4. The computer-implemented method of claim 1 further comprising: receiving feedback from the medical professional and incorporating the feedback into the cognitive engine for at least one of a future cognitive diagnostic and a future recommendation.

5. The computer-implemented method of claim 1,
wherein said at least one visual image sensor is selected from a group consisting of an infrared camera and an ultraviolet camera;
wherein said at least one IoT sensor includes a timer, a clock, a gyroscope, an accelerometer, a tactile sensor, a chemical sensor, a thermometer, a pH sensor, a bacterial sensor, a nutrient sensor, a sensor capable of identifying concentrations of hydrogen sulfide, methyl mercaptan, dimethyl sulfide, cadaverine, putrescine, and skatole, and a sensor of user consumption for the personal daily oral care device,
wherein the at least one IoT sensor and the at least one visual image sensor have a power source that is a biology-enabled generator;
wherein the at least one IoT sensor and the at least one visual image sensor are both biology enabled, and
wherein said at least one personal daily oral care device is a multi-sensor enabled oral irrigator.

6. The computer-implemented method of claim 1, further comprising generating an alert to the user in response to at least one of identifying areas of neglect in the oral healthcare regimen and identifying physiological abnormalities within the oral cavity.

7. The computer-implemented method of claim 5, further comprising modifying at least one personal oral care device to operatively couple the at least one IoT sensor and the at least one visual image sensor such that the at least one IoT sensor and the at least one visual image sensor are both reversibly attached to the oral irrigator and such that the at least one personal oral care device is capable of capturing the length of time the device is used and the angle and location where the device is focused.

8. The computer-implemented method of claim 1,
wherein the identifying of the physiological abnormalities within the oral cavity identifies whether tooth movement has stopped for a user wearing braces,
wherein an alert is automatically issued in response to a positive identification, and
wherein the performing of the real-time analysis and cognitive diagnostics over time diagnoses that braces need to be adjusted in response to a positive identification that the tooth movement has stopped.

9. The computer-implemented method of claim 1,
wherein the identifying of the physiological abnormalities within the oral cavity identify whether teeth are moving back to original problem positions for a user who previously wore braces,
wherein an alert is automatically issued in response to a positive identification, and
wherein the performing of the real-time analysis and cognitive diagnostics over time diagnoses that the user who previously wore braces is not wearing a retainer in response to a positive identification that the teeth are moving back into original problem positions.

* * * * *